United States Patent [19]
do Céu Goncalves da Costa et al.

[11] Patent Number: 5,440,050
[45] Date of Patent: Aug. 8, 1995

[54] PROCESS FOR THE MANUFACTURE OF SPIROKETALS

[75] Inventors: Maria do Céu Gonçalves da Costa, Lisbon; Maria J. V. de Oliveira Baptista Marcelo Curto, Oeiras; Maria R. de Loureiro da Silva Tavares da Rosa, Parede, all of Portugal; William B. Motherwell, Twickenham, United Kingdom

[73] Assignee: Givaudan-Roure Corporation, Clifton, N.J.

[21] Appl. No.: 325,560

[22] Filed: Oct. 18, 1994

Related U.S. Application Data

[63] Continuation of Ser. No. 987,278, Mar. 9, 1993, abandoned filed as PCT/EP92/01601, Jul. 15, 1992.

[30] Foreign Application Priority Data

Jul. 17, 1991 [PT] Portugal .................................. 98344

[51] Int. Cl.⁶ .............................................. C07D 311/78
[52] U.S. Cl. ................................ 549/383; 549/332; 549/525
[58] Field of Search .................. 549/383, 332, 525

[56] References Cited

U.S. PATENT DOCUMENTS

| | | | |
|---|---|---|---|
| 3,144,465 | 8/1964 | Ruzicka et al. | 549/332 |
| 4,276,216 | 6/1981 | Hajos et al. | 549/525 |

FOREIGN PATENT DOCUMENTS 428765  7/1967  Switzerland .

OTHER PUBLICATIONS

Dey et al "The Conversion of Eperuic Acid into Ethers of the enantio-14,15-Di norlabdane Series." Helv. Chim. Acta, vol. 61, No. 3, (1978) pp. 1004–1010.

White et al "Lewis Acid and Photochemically Mediated Cycuzation of Olefinic β-Keto Esters" J. Org. Chem., vol. 50, (1985), pp. 1939–1948.

(List continued on next page.)

Primary Examiner—Richard L. Raymond
Assistant Examiner—Mary C. Cebulak

Attorney, Agent, or Firm—George M. Gould; George W. Johnston; Mark E. Waddell

[57] ABSTRACT

A process for the production of ambergris-type labdane spiroketals of general formulae I and II

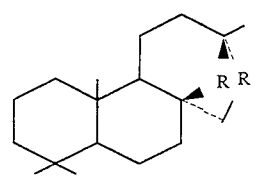

and/or

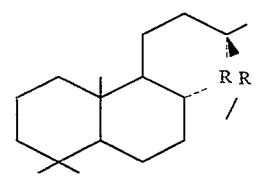

where R represents oxygen or sulphur, useful in the perfumery industry, the said process being characterized by the intramolecular cyclisation of the epoxyketone or its thio analog of general formula III

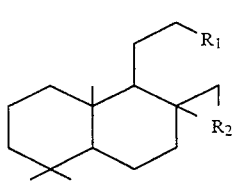

where $R_1$ represents $COCH_3$ and $R_2$ oxygen or sulphur.

11 Claims, No Drawings

OTHER PUBLICATIONS

Fotsch et al "Stereochemical Control in Reactions of Nucleophiles with Oxocarbenium Ions Formed by, etc." J. Org. Chem., vol. 56, (1991), pp. 4141-4147.
Carey et al, Advanced Organic Chemistry, Part B: Reactions and Synthesis, N.Y., Plenum Press, 1990, p. 625.
Moeller, T "Inorganic Chemistry: A Modern Introduction", N.Y., Wiley-Inter-Science, 1982, p. 601.
G. Ohloff "Fragrance Chemistry: The Science of the Sense of Smell", E. T. Theimer (Ed.), Academic Press, N.Y. (1982) 535-573.
A. Boix Camps, Perfumer & Flavorist, 10, 15 (1985).
E. Demole et al., Helv. Chim. Acta 50 1314 (1967).
I. B. Bersuker et al., Nouv. J. Chemie, 9, 211 (1985).
G. Ohloff et al., Helv. Chim. Acta, 63, 1932 (1980).
H. R. Schenk et al., Helv. Chim.Acta, 35, 817 (1952).
E. Demole, Experientia, 20, 609 (1964).
P. K. Grant et al., J. Chem. Soc., Notes, 5274 (1960).
P. K. Grant et al., Tetrahedron, 30, 2386-2395 (1974).
P. F. Vlad, Russian Chemical Reviews, 51, 644 (1982).
J. de Pascual et al., Anales de Quimica, 80, (1984) 280-2.
P. Martres et al., Tetrahedron Letters, 32 (1991) 765-6.
Poster paper presented by M. do Céu Costa et al., at Int. Conf. "Chemistry of Flavours and Fragrances", Canterbury, U.K. on Jul. 17, 1991.
Abstract available Jul. 16, 1991—Poster paper presented by M. do Céu Costa et al., at Int. Conf. "Chemistry of Flavours and Fragrances", Canterbury, U.K. on Jul. 17, 1991.

PROCESS FOR THE MANUFACTURE OF SPIROKETALS

This is a continuation of U.S. application Ser. No. 07/987,278, filed Mar. 9, 1993, abandoned filed as PCT/EP92/01601, Jul. 15, 1992.

This invention describes a new process for the preparation of ambergris-type labdane spiroketals of the general formulae

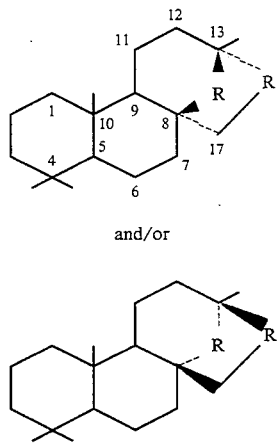

and/or where R represents oxygen or sulphur.

The labdane spiroketals of general formulae I and II, preferably II, where R=O are highly valued in the perfumery industry because of their intense and lasting fragrance [G. Ohloff, in "Fragrance Chemistry: The Science of the Sense of Smell", E. T. Theimer (Ed.), Academic Press, N.Y., 1982, p.535-573] and are used as ingredients in the formulation of high quality perfumes [A. Boix Camps, Perfumer & Flavourist, 10, 15 (1985)]. However, it is known that the spiroketal I with R=O is odorless [E. Demole and H. West, Helv. Chim. Acta 50, 1314 (1967); I. B. Bersuker et al., Nouv. J. Chemie, 9, 211 (1985)] and that spiroketal II with R=O has a strong ambergris fragrance [G. Ohloff, C. Vial, H. R. Wolkf, K. Job, E. Jégou, J. Polonsky and E. Lederer, Helv. Chim. Acta, 65, 1932 (1980)].

The industrial processes for the production of these compounds generally start from sclareol and manool, and yield mixtures of the oxygenated spiroketals I and II (R=O). The preparation of I and II (R=O) was first described by Schenk et al. [H. R. Schenk, H. Gutmann, O. Jeger and L. Ruzicka, Helv. Chim. Acta, 35,817 (1952)] and L. Ruzicka et al., U.S. Pat. No. 3,144,465 (1964) for the synthesis of a mixture of the oxygenated spiroketals I and II (R=O) starting from manool, by the expoxidation with peracetic, perbenzoic, monoperphthalic, percamphoric or performic acids, followed by oxidation, preferably with osmium tetroxide and sodium methaperiodate. A further process also described [E. Demole, Experientia, 20, 609 (1964)] the semi-industrial production of a mixture of the oxygenated spiroketals I and II (R=O) starting from manool, which combines the epoxidation by perbenzoic acid with the ozonolysis of the resulting epoxide, the products thus obtained being then treated with p-toluenesulphonic acid. These methods lead to mixtures of the spiroketals I and II (R=O) in yields not higher than 30% and have the disadvantage of using toxic and/or expensive reagents, as well as the added disadvantage of producing mixtures of compounds in which one of the components is odorless, thereby reducing the commercial value of the final product for the application in the industry of perfumery.

The process of the present invention allows the stereospecific and stereoselective production of compounds I and II and can use as starting material the labdane diterpenes of general formula

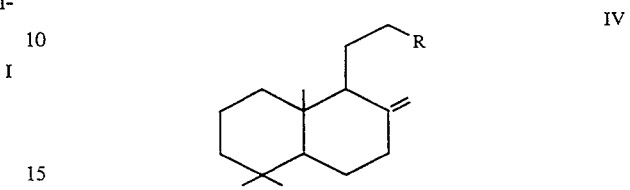

where R is a allylic tertiary alcohol or a optionally alkyl esterfied vinyl acid residue, in particular R=C(CH₃)=CHCOOR' or C(CH₃)(OH)CH=CH₂ with R'=$C_nH_{2n+1}$ or H, and where n=1-5, including thus the acids anticopalic (E-form) and copalic (Z-form) or its corresponding alkyl esters, or manool, or predecessors such as sclareol as starting materials, through the common intermediate

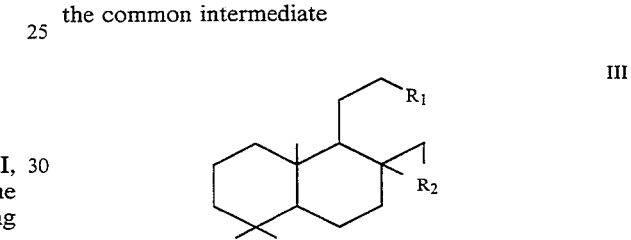

or preferably

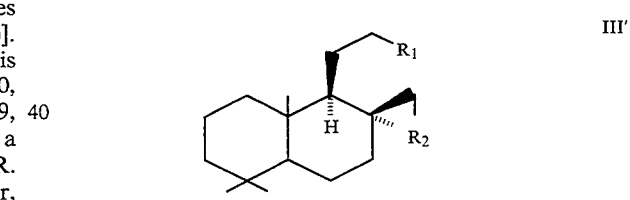

where R1=COCH₃ and R₂ represents oxygen or sulphur.

This method allows producing from the compound of the general formula IV, with yields of 70-90%, exclusively the oxygenated compound of formula II or, if desired, mixtures enriched with said fragrant compound II.

The oxidation of anticopalic acid IV (R=E—C(CH₃)=CHCOOH) with an oxidizing agent, e.g. a permanganate, such as potassium permanganate, in the presence of a conventional phase-transfer catalyst, in particular of the quaternary ammonium salt type, leads to the 14, 15-dinorlabdan-8, 17-en-13-one

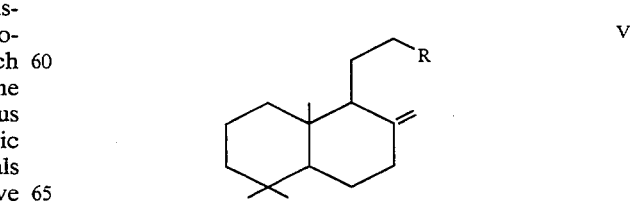

where R=COCH₃, in yields up to 90%, the same intermediate V being also obtained under similar conditions from manool, but in higher yields and with reaction times substantially shorter than those described in the literature [H. R. Schenk, H. Gutmann, O. Jeger and L. Ruzicka, Helv. Chim. Acta 35, 817–824 (1952); P. K. Grant and R. Hodges, J. Chem. Soc. 5274 (1960); P. K. Grand and R. T. Weavers, Tetrahedron, 2386–2395 (1974); P. F. Vlad, Russian Chem. Rev. 51,644 (1982)].

The epoxidation of V with a peracid, such as m-chloroperbenzoic acid, under reaction conditions compatible with the species III which is unstable in acid medium, leads to the epoxyketone 8α, 17-epoxy-14,15-dinorlabdan-13-one (III, $R_2$=O) stereoselectively and in yields greater than 80%. The epoxyketone (III, $R_2$=O) can be converted in high yields into the thiirane (III, $R_2$=S) by treatment with a sulphurating agent, such as triphenylphosphine sulfide or thiazolidine-2-thione.

The treatment of the epoxyketone III involving an intramolecular cyclisation or ketalisation can be generally effected a) with organic protonic acids, such as p-toluenesulphonic acid—which embodiment is not part of the invention, or a') with Lewis acids, such as zinc chloride, or its complexes, e.g. etherates, Mg salts, $Cu^{2+}$ salts, etc., in homogeneous medium, in catalytic or stoichiometric amounts, or b) with mineral or organic protonic acid or Lewis acid catalysts (such as listed above), such as oxalic acid, etc., in heterogeneous phase, i.e. on appropriate supports, e.g. on a microporous solid, e.g. a sheet or phyllosilicate, or a tectosilicate, e.g. a clay, e.g. on aluminosilicates of substantial magnesium oxide content, e.g. vermiculite, montmorillite, a HY zeolite [a Y type zeolite in acid form], silicalite, silica, alumina or on another microporous solids with comparable cristallographical characteristics, and also on supports such as sulphonic ion exchange resins, in the presence or absence of an organic solvent, e.g. an optionally halogenated aliphatic or aromatic hydrocarbon, such as hexane, methylene or ethylene chloride, preferably at room temperature or at elevated temperatures, e.g. up to the boiling point of the reaction mixture.

When using Lewis acids, the use of a solvent is indicated.

The activation of the support is well known per se; one usually prepares a suspension of the support in—any of the above mentioned—acids, then follows a washing step, and then, preferably, a drying step. Optimum activity of the obtained material can be established by means of a few experiments.

The same applies when using the heat treatment for the activation, the preferred temperature range being ca. 100° C. to ca. 240° C.

To ensure the predominant formation of spiroketal II (e.g. R=O), the oxygen atoms of the carbonyl group and of the epoxide grouping of compound III have to be complexed to the same catalytic site (atom, ion) in order to fix (to complex) the desired conformation enabling the intended internal cyclisation. This prerequisite is alsways fulfilled by the inventive method described here.

The process of the present invention is illustrated in the following Examples, where the process is described using as starting material anticopalic acid, methyl anticopalate and manool.

EXAMPLE 1 (IV→V)

14,15-DINORLABDAN-8,17-EN-13-ONE (V, R=COCH$_3$) FROM ANTICOPALIC ACID OR METHYL ANTICOPALATE

To a solution of potassium permanganate (700 mg) in water (7.5 ml) was added benzene (4 ml) followed by benzyltriethylammonium chloride (180 mg). To this mixture was added with permanent stirring a suspension of anticopalic acid (230 mg) in benzene (1 ml) and heated to 35°–50° C. for 1.5 hours. The excess permanganate was destroyed, the mixture acidified with diluted hydrochloric acid the organic phase separated, washed and dried. Removal of the solvent at reduced pressure gave a colourless oil (368.8 mg) which was purified bu. chromatography on silica to afford 14,15-dinorlabdan-8.17-en- 13-one as an oil (203.4 mg; 88 % ). $[\alpha]D^{20}+22°$ (c. 0.01 mg, CDCl$_3$) $\nu_{max}$1710 (C=O), 1635 (C=C)cm$^{-1}$; $\delta^1$H (CDCl$_3$): 0.67 (3H, s, 20-CH$_3$), 0.78 (3H, s, 19-CH$_3$), 0.85 (3H, s, 18-CH$_3$), 2.09 (3H, s, COCH$_3$), 4.81 and 4.42 ppm (2H, 2s, =CH$_2$); m/z 262 (M$^-$), 247 (M-15), 219, 137, 104, 69, 43. Under identical conditions the same product is obtained from methyl anticopalate.

EXAMPLE 2 (IV→V)

14,15-DINORLABDAN-8,17-EN-13-ONE (V, R=COCH$_3$) FROM MANOOL

To a solution of manool (2.9 g) in dichloromethane (20 ml) at 0°–20° C. was slowly added a suspension of potassium permanganate (3.1 g) and benzyltriethylammonium chloride (4.5 g) in dichloromethane (90 ml). The mixture was kept at 0°–3° C. for 8 hours, acidified with concentrated hydrochloric acid and the excess permanganate destroyed by addition of an aqueous solution of sodium sulphite. The organic phase was separated, washed with water, dried and concentrated at reduced pressure to afford an oil (2.72 g) containing 90% of 14, 15-dinorlabdan-8, 17-en- 13-one, which was purified by chromatography and characterised by physical and spectroscopic data (see Example 1 ).

EXAMPLE 3 (V→III)

8α,17-EPOXY-14,15-DINORLABDAN-13-ONE (III, $R_1$=COCH$_3$, $R_2$=O)

A solution of 14,15-dinorlabdan-8,17-en-13-one (71.7 mg)in dichloromethane (18 ml) was added to a 0.5M aqueous solution of sodium bicarbonate (8.0 ml) followed by slow addition of m-chloroperbenzoic acid (79.0 mg) with stirring at room temperature. After 24 h, the reaction mixture was washed successively with aqueous sodium sulphide, sodium bicarbonate and water, the organic phase separated, dried and concentrated at reduced pressure to afford 8α,17-epoxy-14,15-dinorlabdan-13-one (111, R=COCH$_3$) as an oil (86%), $\delta^1$H (CDCl$_3$): 0.82 (3H, s, 20-CH$_3$), 0.82 (3H, s, 19-CH$_3$), 0.89 (3H, s, 18-CH$_3$), 2.10 (3H, s, COCH$_3$), 2.43–2.50 (2H, m, CH$_2$COCH$_3$), 2.81 (1H, d, J=4.3, CH$_2$O), 2.82 ppm (1H, $\overline{dd}$, J=4.3 ;J=1.25, CH$_2$O), m/z 278 (M$^+$.).

EXAMPLE 4 (III→I, II)

8,13-EPITHIOEPOXY-13,17-OXIDO-14,15-DINORLABDANES (I and II, 8, 13R=S and 13,17R=O)

To a solution of 8α, 17-epoxy-14,15-dinorlabdan-13-one (39 mg) and triphenylphosphine sulphide (41 mg) in dry benzene (0.5 ml) was added trifluoroacetic acid (0.1 ml) at 20°–25° C. with stirring. After 10 min anhydrous sodium carbonate was added and stirring was kept for a further 15 min, and the mixture was filtered to afford a crude product containing the oxygenated spiroketals II (R=O) (60%), $\delta^1$H: 0.80 (3H, s, 19-CH$_3$), 0.89 (6H, s, 20-CH$_3$ and 18-CH$_3$), 1.41 (3H, s, 16-CH$_3$), 3.35 (1H, d, J=7.5, 17-CH$_2$); 4.30 ppm (1H, d, J=7.5, 17-CH$_2$); and I (R=O) (5%) $\delta^1$H: 0.87 (3H, s, 20-CH$_3$), 0.88 (3H, s, 19-CH$_3$), 1.09 (3H, s, 16-CH$_3$), 1.43(3H, s, 18-CH$_3$), 3.32 (1H, d, J=6.6, 17-CH$_2$), 3.77 ppm (1H, d, J =6.6, 17-CH$_2$), the epithiospiroketal I (8,13R=S and 13,17R=O) (8%), $\delta^1$H (CDCl$_3$): 3.76 (1H, d, J=7.5, 17-CH$_2$), 3.33 (1H, d, J=7.2,17-CH$_2$), 1.41 (3H, s, 18-CH$_3$), 1.09 (3H, s, 16-CH$_3$), 0.88 ppm (6H, s, 17-CH$_3$ and 20-CH$_3$), m/z 294 (M+.) and epithiospiroketal II (8,13R=S and 13,17R=O) (23.4%) $\delta^1$H (CDCl$_3$): 0.80 (3H, s, 19-CH$_3$), 0.88 (6H, s, 20-CH$_3$ and18-CH$_3$), 1.41 (3H, s, 16-CH$_3$), 3.37 (1H, d,J=7.5, 17-CH$_2$), 4.31 ppm(1H, d, J=7.5, 17-CH$_2$), m/z294 (M+.), 218 (100.0).

EXAMPLE 5 (III→II)

8',13; 13, 17-DIOXI-14,15-DINORLABDANE (II, R=O)

5.1 IN HOMOGENEOUS PHASE WITH ACID

Epoxyketone III (R$_1$=COCH$_3$, R$_2$=O) (4.3 mg) was dissolved in dichloromethane (2 ml) and zinc chloride was added (8.8 mg). After 1 hour at room temperature, the mixture was washed with water, the organic phase separated, dried and concentrated at reduced pressure to afford spiroketal II (R=O) (97%) as an oil, $\delta^1$H (CDCl$_3$): 0.80 (3H, s, 19-CH$_3$), 0.89 (6H, s, 20-CH$_3$ and 18-CH$_3$), 1.41 (3H, s, 16-CH$_3$), 3.35 (1H, d, J=7.5, 17-CH$_2$), 4.30 ppm (1H, d, J=7.5, 17-CH$_2$), m/z 278 (M+.).

5.2. IN HETEROGENEOUS PHASE WITH A SOLID THERMICALLY ACTIVATED SUPPORT AND IN THE PRESENCE OF SOLVENT

A solution of epoxyketone III (R$_1$=COCH$_3$, R$_2$=O) ( 10 mg) in dry n-hexane (5 ml) was added at 18°-25° C. to a flask containing activated vermiculite. After transformation of the starting material, the solution was filtered and the residual vermiculite washed with n-hexane. The filtrate was dried and concentrated at reduced pressure to afford the spiroketal II (R=O) (90%), $\delta^1$H (CDCl$_3$): 0.80 (3H, s, 9-CH$_3$), 0.89 (6H, s, 20-CH$_3$ and 18-CH$_3$), 1.41 (3H, s, 16-CH$_3$), 3.35 (1H, d, J =7.5, 17-CH$_2$), 4.30ppm (1H, d, J=7.5, 17-CH$_2$) and spiroketal I (R=O) (5%), $\delta^1$H (CDCl$_3$): 0.87 (3H, s, 20-CH$_3$), 0.88 (3H, s, 19-CH$_3$), 1.09 (3H, s, 16-CH$_3$), 1.43 (3H, s, 18-CH$_3$), 3.32 (1H, d, J=6.6, 17-CH$_2$), 3.77 ppm (1H, d, J=6.6, 17-CH$_2$).

5.3. The mode is as in 5.2.

To a solution of epoxyketone III (R$_1$=COCH$_3$, R$_2$=O) (1 g) in dry dichloromethane (50 ml) was added 1 g of montmorillonite (type K 10) at a temperature of 18° to 25° C. and the mixture stirred. After complete transformation of the starting material (GC control) the solid was filtered off and the filtrate evaporated to give 0,9 g of a product containing the spiro ketals II and I in a ratio of 90:10.

EXAMPLE 6 (III→I)

8β, 13; 13, 17-DIEPOXI-14, 15-DINORIABDANE ((I, R=O)

6.1 IN HOMOGENEOUS PHASE WITH ACID

To a solution of epoxyketone III (R$_1$=COCH$_3$, R$_2$=O) (10 mg) in dry toluene (2–5ml) was added anhydrous p-toluenesulphonic acid (7 mg) and the mixture kept at room temperature with stirring for a few hours, or heated immediately to reflux until complete disappearance of the starting material, to produce quantitatively the spiroketal 8β, 13; 13, 17-diepoxi-14, 15-dinorlabdane I (R=O) identified by proton nuclear magnetic resonance and mass spectrometry (see 6.2).

6.2 IN HETEROGENEOUS PHASE WITH A SOLID SUPPORT (THERMICALLY ACTIVATED) AND IN THE ABSENCE OF SOLVENT

The catalyst (silica gel 230–400 mesh, 0.4 g; neutral aluminium oxide, Brockmann, activity I, 150 mesh, 50 Å, 0.4 g; silicalite 0.5 g; basic alumina, activity I, 230–400 mesh, I g; activated vermiculite, 0.1 g) was added to a solution of epoxyketone III ((R$_1$=COCH$_3$, R$_2$=O) (6 mg) in dry petroleum ether (3 ml), the solvent removed and the mixture heated to 150°–200° C. for 1–4 hours. Addition of solvent, filtration of the suspension and concentration of the filtrate produced the spiroketal I (R=O) as an oil (6.0 mg; 100%), $\delta^1$H (CDCl$_3$): 0.87 (3H, s, 20-CH$_3$), 0.88 (3H, s, 19-CH$_3$), 1.09 (3H, s, 16-CH$_3$), 1.43 (3H, s, 18-CH$_3$), 3.32 (1H, d, J=6.6, 17-CH$_2$), 3.77 ppm (1H, d, J=6.6, 17-CH$_2$).

EXAMPLE 7

8β, 13; 13, 17-DIEPOXI-14, 15-DINORLABDANE (I, R=O) and 8α, 13; 13, 17-DIEPOXI-14, 15-DINORLABDANE (II, R=O)

To a suspension of silica gel 60 (230–400 mesh, 0.11 g) in dichlormethane (0.5 ml) was added a 10% aqueous solution of the acidic activator oxalic acid (0.8 ml) and a solution of epoxyketone III (R$_1$=COCH$_3$, R$_2$=O) (2.4 mg) in dichloromethane (1 ml). After the reflux for 24 hours, the reaction mixture was treated with sodium bicarbonate, the organic phase separated, dried and concentrated to afford a mixture of spiroketals I (R=O) (25%) and II (R =O) (70%), identified by comparison with authentic samples.

We claim:

1. A process for the manufacture of mixtures of compounds of the general formulae I and II in yields of at least 70%

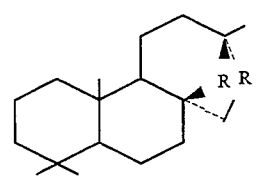

and/or

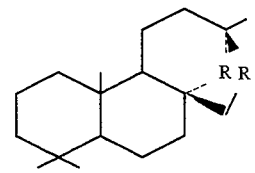

wherein the mixture comprises compound II in yields of at least 70%, and R represents oxygen, said process comprising the intramolecular cyclisation or ketalisation of the epoxyketone of general formula III

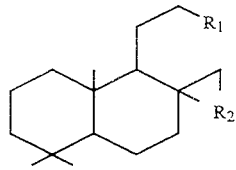

where $R_1 = COCH_3$ and $R_2$ represents oxygen, effected by a solid catalyst activated by acid, or by heat treatment, or by a Lewis acid catalyst with the exception of $BF_3$ or its complexes, and in the presence or absence of an organic solvent, at room temperature or at elevated temperatures, where the solid catalyst is a microporous solid, which is a sheet or phyllosilicate, or a tectosilicate, selected from the group consisting of clay, vermiculite. montmorillite, HY zeolite, silicalite, or another microporous solid with comparable crystallographical characteristics.

2. A process according to claim 1, where the preferred solid catalyst is high in magnesium oxide content, e.g. vermiculite, and the solvent is n-hexane, to produce practically quantitatively II.

3. A process according to claim 2, where the solid catalyst is heat-activated under vacuum at ca.100°-ca.250° C.

4. A process according to claim 1, where said solid acid catalyst reacts in an organic solvent at room temperature to produce quantitatively II.

5. A process according to claim 1, where the solid catalyst is activated by an acid and reacts in an organic solvent, preferably at reflux temperature, to produce mixtures rich in II (e.g. >60%).

6. A process according to claim 1, where the compound III is prepared by epoxidation of the compound

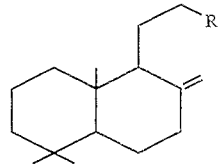

where $R=COCH_3$,
using a peracid, preferably m-chloroperbenzoic acid, in buffered medium.

7. A process according to claim 6, where the preferred buffering agent is sodium bicarbonate.

8. A process according to claim 6, where V is obtained by permanganate oxidation with phase-transfer catalysis and with pH control from a labdane diterpene of general formula IV

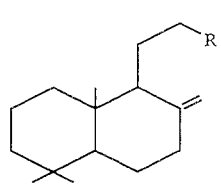

where R is an allylic tertiary alcohol or a optionally alkyl esterified vinyl acid residue.

9. A process according to claim 8, where IV is anticopalic acid, copalic acid or one of their esters.

10. A process according to claim 9, where the ester is the methyl ester.

11. A process according to claim 1, wherein said compound II is produced in a yield of at least 90%.

* * * * *